US008865115B2

(12) United States Patent
Bechtloff et al.

(10) Patent No.: US 8,865,115 B2
(45) Date of Patent: Oct. 21, 2014

(54) PROCESS FOR THE PREPARATION OF NANOPARTICULATE ZINC OXIDE

(75) Inventors: Bernd Bechtloff, Ludwigshafen (DE); Lars Vicum, Heidelberg (DE); Hartwig Voβ, Frankenthal (DE); Robert Wengeler, Karlsruhe (DE); Andrey Karpov, Mannheim (DE); Jing Dreher, Stuttgart (DE); Valerie Andre, Ludwigshafen (DE)

(73) Assignee: BASF SE Ludwigshafen (DE)

( * ) Notice: Subject to any disclaimer, the term of this patent is extended or adjusted under 35 U.S.C. 154(b) by 363 days.

(21) Appl. No.: 13/058,020

(22) PCT Filed: Jul. 30, 2009

(86) PCT No.: PCT/EP2009/059896
§ 371 (c)(1),
(2), (4) Date: Feb. 8, 2011

(87) PCT Pub. No.: WO2010/018075
PCT Pub. Date: Feb. 18, 2010

(65) Prior Publication Data
US 2011/0152433 A1    Jun. 23, 2011

(30) Foreign Application Priority Data
Aug. 13, 2008    (EP) .................................. 08162286

(51) Int. Cl.
C09C 1/04 (2006.01)
B82Y 5/00 (2011.01)
A61Q 17/00 (2006.01)
B82Y 30/00 (2011.01)
A61K 8/27 (2006.01)
A61K 8/19 (2006.01)
C09C 1/02 (2006.01)

(52) U.S. Cl.
CPC ... *C09C 1/02* (2013.01); *B82Y 5/00* (2013.01); *A61Q 17/005* (2013.01); *A61K 2800/413* (2013.01); *B82Y 30/00* (2013.01); *C09C 1/043* (2013.01); *A61K 8/27* (2013.01); *A61K 8/19* (2013.01); *C01P 2004/64* (2013.01); *Y10S 977/811* (2013.01)
USPC .......................................... 423/622; 977/811

(58) Field of Classification Search
USPC ......................................... 423/622; 977/811
See application file for complete search history.

(56) References Cited

U.S. PATENT DOCUMENTS

| 2004/0241085 A1* | 12/2004 | Marx et al. ..................... 423/622 |
| 2007/0154709 A1* | 7/2007 | Koch et al. ..................... 428/379 |
| 2007/0243145 A1 | 10/2007 | Andre |
| 2008/0193759 A1* | 8/2008 | Rieger et al. .................. 428/402 |
| 2010/0119829 A1 | 5/2010 | Karpov et al. |

FOREIGN PATENT DOCUMENTS

| DE | 10 2005 025972 A1 | 12/2006 |
| DE | 102005025972 | * 12/2006 |
| WO | WO 2005070820 A1 * | 8/2005 |

OTHER PUBLICATIONS

Heidi Van den Rul, Dirk Mondelaers, Marlies K. Van Bael, Jules Mullens; "Water-based wet chemical synthesis of (doped) ZnO nanostructures"; Journal of Sol-Gel Science and Technology Jul. 2006, vol. 39, Issue 1, pp. 41-47.*

* cited by examiner

Primary Examiner — Richard M Rump
(74) Attorney, Agent, or Firm — Shruti Costales (57) ABSTRACT

The present invention relates to a process for the preparation of nanoparticulate zinc oxide in the form of aqueous suspensions or in the form of pulverulent solid. Furthermore, the invention relates to the use of zinc oxide particles and suspensions prepared in this way in cosmetic sunscreen preparations, as stabilizer in plastics, in paints, in coatings and as antimicrobial active ingredient.

10 Claims, 1 Drawing Sheet

PROCESS FOR THE PREPARATION OF NANOPARTICULATE ZINC OXIDE

The present invention relates to a process for the preparation of nanoparticulate zinc oxide in the form of aqueous suspensions or in the form of solids in powder form. Furthermore, the invention relates to the use of the zinc oxide particles and suspensions prepared by this process in cosmetic sunscreen preparations, as stabilizer in plastics, in paints, in coatings and as antimicrobial active ingredient.

Within the context of the present invention, "particles" are to be understood as meaning primary particles, i.e. not agglomerated particles.

Within the context of the present invention, the term "nanoparticles" is used to refer to particles with an average diameter from 1 to 500 nm, preferably from 5 to 200 nm, determined by means of customary methods known to the person skilled in the art, such as, for example, electron microscopy or light scattering.

Nanoparticulate zinc oxide with particle sizes below ca. 100 nm is potentially particularly suitable for use as UV absorber in cosmetic sunscreen compositions, transparent organic-inorganic hybrid materials, plastics, paints and coatings. In addition, a use to protect UV-sensitive organic pigments, as stabilizer in plastics and as antimicrobial active ingredient is also possible.

A particularly desirable property of zinc oxide particles which are to be used as UV absorbers is in any case the highest possible transparency in the visible wavelength region and the highest possible absorption in the region of near ultraviolet light (UV-A region, ca. 320 to 400 nm wavelength).

Nanoparticulate zinc oxide with particle sizes below ca. 5 nm exhibits, on account of the size quantization effect, a blue shift in the absorption edge (L. Brus, J. Phys. Chem. (1986), 90, 2555 to 2560) and is therefore less suitable for use as UV absorbers in the UV-A region.

The preparation of finely divided zinc oxide by dry and wet processes is known in the art. The classical method of burning zinc, which is known as the dry process (e.g. Gmelin volume 32, 8th edition, supplementary volume, p. 772 ff.), produces aggregated particles having a broad size distribution. Although in principle it is possible to produce particle sizes in the sub micrometer range by grinding processes, suspensions with average particle sizes in the lower nanometer range are only obtainable from such powders with very great expenditure, because the shear forces which can be achieved are very low.

Finely divided zinc oxide is prepared primarily by wet chemical methods by precipitation processes. Precipitation in aqueous solution generally gives hydroxide -and/or carbonate-containing materials which have to be thermally converted to zinc oxide. The thermal aftertreatment here has an adverse effect on the finely divided nature since the particles are subjected during this treatment to sintering processes which lead to the formation of micrometer-sized aggregates, which can be comminuted again only incompletely by grinding.

DE 199 07 704 describes a nanoparticulate zinc oxide prepared via a precipitation reaction. In the process, the nanoparticulate zinc oxide is prepared starting from a zinc acetate solution through an alkaline precipitation. The centrifuged-off zinc oxide can be redispersed to give a sol by adding methylene chloride.

The zinc oxide suspensions prepared in this way have the disadvantage that they do not have good long-term stability.

WO 00/50503 describes zinc oxide gels which comprise nanoparticulate zinc oxide with a particle diameter of at most 15 nm and which are redispersible to give sols. Here, the solids prepared by basic hydrolysis of a zinc compound in alcohol or in an alcohol/water mixture are redispersed by adding dichloromethane or chloroform. A disadvantage here is that stable suspensions are not obtained in water or in aqueous dispersants.

Chem. Mater. 2000, 12, 2268 to 2274 "Synthesis and Characterization of Poly(vinylpyrrolidone)-Modified Zinc Oxide Nanoparticles" by Lin Guo and Shihe Yang describes the surface coating of zinc oxide nanoparticles with polyvinylpyrrolidone. The disadvantage here is that zinc oxide particles coated with polyvinylpyrrolidone are not dispersible in water.

WO 2004/052327 describes surface-modified nanoparticulate zinc oxides in which the surface modification comprises a coating with an organic acid.

DE-A 10 2004 020 766 discloses surface-modified nanoparticulate metal oxides which have been produced in the presence of polyaspartic acid.

EP 1455737 describes surface-modified nanoparticulate zinc oxides in which the surface modification comprises a coating with an oligo- or polyethylene glycolic acid. Some of these products are very costly to produce and are only suitable for cosmetic applications to a limited degree since they may have only poor skin compatibility.

WO 98/13016 describes the use of surface-treated zinc oxide in cosmetic sunscreen preparations, a surface treatment with polyacrylates also being disclosed. Details regarding the preparation of a zinc oxide treated with polyacrylates are not found.

DE 19950496 describes a process for the preparation of nanoparticle concentrates in which aqueous or alcoholic, if appropriate salt-containing, suspensions of nanoparticles with an average diameter of from 10 to 200, preferably 25 to 150 and in particular 50 to 100 nm are subjected to at least one ultrafiltration and thereby separated into a dilute, if appropriate salt-comprising permeate and a retentate which comprises at least 90% of the nanoparticles used.

It is clear from the preceding description of the prior art that there is a need for processes with which it is possible to prepare surface-modified nanoparticulate zinc oxide particles and their aqueous suspensions, which simultaneously have the highest possible transparency in the visible wavelength region and the highest possible absorption in the region of near ultraviolet light (UV-A region, ca. 320 to 400 nm wavelength). A further object consists in providing suspensions of zinc oxide particles which, based on zinc oxide, comprise the lowest possible concentrations of salts, such as, for example, sodium chloride, and the lowest possible concentrations of free, not adsorbed dispersant.

It was therefore another object of the present invention to provide surface-modified nanoparticulate zinc oxide particles and aqueous suspensions thereof which simultaneously show the highest possible transparency in the visible wavelength region and the highest possible absorption in the region of near ultraviolet light (UV-A region, ca. 320 to 400 nm wavelength) and, in relation to cosmetic applications, particularly in the field of UV protection, are characterized by good skin compatibility. A further object of the present invention was the provision of improved UV protectants for the stabilization of photosensitive materials, in particular plastics. Another object was to provide aqueous suspensions of such nanoparticulate zinc oxide particles which, based on zinc oxide, comprise the lowest possible concentrations of salts, such as, for example, sodium chloride. The aqueous suspensions should be able to be used as far as possible directly for producing cosmetic preparations, i.e. comprise cosmetically inacceptable substances only in low cosmetically acceptable amounts, if at all. Furthermore, it is desirable that the suspensions have the highest possible solids content.

In particular, the zinc oxide particles should satisfy the following conditions:
1) Transmission at a wavelength of 450 nm ($T_{450\,nm}$) of at least 85%, preferably at least 90% and
2) Transmission at a wavelength of 360 nm ($T_{360\,nm}$) of at most 30%, preferably at most 25%.

The quotient $\ln(T_{360\,nm})/\ln(T_{450\,nm})$ should be at least 7, preferably at least 10 and particularly preferably at least 13.

These transmission values can be determined, for example, in accordance with a method as described in EP 1892218 A1, paragraph [0081]. For example, 2 g of zinc oxide particles prepared according to this invention are firstly thoroughly ground in 3 g of castor oil and dispersed using a triple-roll machine. With the help of a doctor blade, a ca. 5 to 10 µm thick film is prepared from the resulting suspension and its transmission is measured using a UV-VIS spectrometer (Hitachi U 3010) in the range from 280 to 800 nm.

In relation to cosmetic applications, particularly in the UV protection sector, the zinc oxide particles and the substances used for their surface modification should in particular be characterized by good skin compatibility. Furthermore, the surface-modified zinc oxide particles must be easy to incorporate into the cosmetic preparations and the resulting preparations must be stable over a period of at least 4 weeks, preferably at least 3 months, particularly preferably at least 6 months, which means that during this period essentially no aggregation of the zinc oxide particles arises which would markedly reduce the UV absorption by the particles.

This object is achieved by a process for the preparation of surface-modified nanoparticulate zinc oxide particles comprising the steps
a) preparation of a solution comprising water and at least one zinc salt (solution 1) and a solution comprising water and at least one strong base (solution 2), where at least one of the two solutions 1 and 2 comprises at least one polyacrylate,
b) mixing the solutions 1 and 2 prepared in step a), during which the surface-modified nanoparticulate particles are formed and precipitate out of the solution to form an aqueous suspension,
c) concentration of the aqueous suspension of the surface-modified nanoparticulate particles obtained in step b), where the pH of the suspension obtained in step b) and to be conveyed to step c) is in a range from 9 to 14,
d) optional purification of the concentrated aqueous suspension of the surface-modified nanoparticulate particles obtained in step c),
e) optional drying of the surface-modified nanoparticulate particles obtained in step d) and
f) optional thermal aftertreatment of the dried, surface-modified nanoparticulate particles obtained in step e) and
g) optional grinding of the particles obtained in step f).

a) Preparation of the Solutions
Solution 1

Solution 1 comprises water and at least one zinc salt. Solution 1 can comprise further ingredients.

Preferred zinc salts are selected from zinc chloride, zinc acetate, zinc sulfate and zinc nitrate, with zinc chloride being particularly preferred.

The concentration of the zinc salt in solution 1 is generally in the range from 0.05 to 2 mol/l, preferably in the range from 0.2 to 1.5 mol/l, particularly preferably 0.3 to 1.0 mol/l.

In one embodiment of the invention, the pH of the aqueous solution of the zinc salt is adjusted prior to mixing to a value in the range from 3 to 6, preferably from 4 to 5.

In one embodiment of the invention, the temperature of the aqueous solution of the zinc salt is adjusted prior to mixing to a value in the range 40° C. to 80° C., preferably from 50° C. to 70° C., particularly preferably from 55° C. to 65° C.

Solution 2

Solution 2 comprises water and at least one strong base. The strong bases present in solution 2 may generally be any desired substances which are able to produce a pH of from about 8 to about 13, preferably from about 9 to about 12.5, in aqueous solution depending on their concentration.

These may be, for example, metal oxides or hydroxides and also ammonia or amines. Preference is given to using alkali metal hydroxides such as sodium hydroxide or potassium hydroxide, alkaline earth metal hydroxides, such as calcium hydroxide or ammonia.

Particular preference is given to using sodium hydroxide, potassium hydroxide and ammonia.

In one embodiment of the invention, ammonia can also be formed through thermal decomposition of urea in situ during process steps a) and/or b).

The concentration of the strong base in solution 2 prepared in process step a) is preferably chosen so that a hydroxyl ion concentration in the range from 0.1 to 4 mol/l, particularly preferably from 0.4 to 3 mol/l and in particular from 0.6 to 2 mol/l is established in solution 2.

Preferably, the hydroxyl ion concentration in solution 2 ($c(OH^-)$) is chosen to be approximately twice as high as the concentration of the zinc ions in solution 1 ($c(Zn^{2+})$). For example, in the case of a solution 1 with a concentration of zinc ions of about 0.2 mol/l, preferably a solution 2 with a hydroxyl ion concentration of about 0.4 mol/l is used.

Polyacrylate

According to the invention, the polyacrylates are polymers based on at least one $\alpha,\beta$-unsaturated carboxylic acid, for example acrylic acid, methacrylic acid, dimethacrylic acid, ethacrylic acid, maleic acid, citraconic acid, methylenemalonic acid, crotonic acid, isocrotonic acid, fumaric acid, mesaconic acid and itaconic acid. Preferably, polyacrylates based on acrylic acid, methacrylic acid, maleic acid or mixtures thereof are used.

The fraction of the at least one copolymerized $\alpha,\beta$-unsaturated carboxylic acid in the polyacrylate is preferably in the range from 20 to 100 mol %, further preferably in the range from 50 to 100 mol %, particularly preferably in the range from 75 to 100 mol %.

The polyacrylates can be used either in the form of the free acids or else partially or completely neutralized in the form of their alkali metal, alkaline earth metal or ammonium salts. They can, however, also be used as salts of the respective polyacrylate with the organic bases triethylamine, ethanolamine, diethanolamine, triethanolamine, morpholine, diethylenetriamine, dimethylethanolamine, 2-amino-2-methyl-1-propanol or tetraethylenepentamine.

Besides the at least one $\alpha,\beta$-unsaturated carboxylic acid, the polyacrylates can also comprise further comonomers in copolymerized form. Further suitable comonomers are, for example, the esters, amides and nitriles of the aforementioned carboxylic acids, e.g. methyl(meth)acrylate, ethyl(meth)acrylate, hydroxyethyl(meth)acrylate, hydroxypropyl(meth)acrylate, hydroxybutyl(meth)acrylate, hydroxyisobutyl(meth)acrylate, monomethyl maleate, dimethyl maleate, monoethyl maleate, diethyl maleate, 2-ethylhexyl(meth)acrylate, (meth)acrylamide, N,N-dimethylacrylamide, N-tert-butylacrylamide, (meth)acrylonitrile, dimethylamino-ethyl(meth)acrylate, diethylaminoethyl(meth)acrylate, dimethylaminopropylmethacrylamide, and the salts of the last-mentioned basic monomers with carboxylic acids or mineral acids, and also the quaternized products of the basic (meth) acrylates and -amides.

Further suitable copolymerizable comonomers are allylacetic acid, vinylacetic acid, acrylamidoglycolic acid, vinylsulfonic acid, allylsulfonic acid, methallylsulfonic acid, styrenesulfonic acid, 3-sulfopropyl acrylate, 3-sulfopropyl methacrylate or acrylamidomethylpropanesulfonic acid, and also monomers comprising phosphonic acid groups, such as vinylphosphonic acid, allylphosphonic acid or acrylamidomethanepropanephosphonic acid. The monomers comprising acid groups can be used in the polymerization in the form of the free acid groups and also in partially or completely base-neutralized form.

Further suitable copolymerizable compounds are N-vinylcaprolactam, N-vinylimidazole, N-vinyl-2-methylimidazole, N-vinyl-4-methylimidazole, vinyl acetate, vinyl propionate, N-vinylpyrrolidone, isobutene or styrene, and also compounds with more than one polymerizable double bond, such as, for example, diallylammonium chloride, ethylene glycol dimethacrylate, diethylene glycol diacrylate, allyl methacrylate, trimethylolpropane triacrylate, triallylamine, tetraallyloxyethane, triallyl cyanurate, diallyl maleate, tetraallylethylenediamine, divinylideneurea, pentaerythritol di-, pentaerythritol tri- and pentaerythritol tetraallyl ethers, N,N'-methylenebisacrylamide or N,N'-methylenebismethacrylamide.

It is of course also possible to use mixtures of said comonomers. For example, mixtures of 50 to 100 mol % of acrylic acid and 0 to 50 mol % of one or more of the aforementioned comonomers are suitable for the preparation of the polyacrylates according to the invention.

Numerous polyacrylates suitable for the process according to the invention are commercially available under the name Sokalan® (BASF).

According to the invention, the polyacrylates may be present in one of the solutions 1 or 2 or in both solutions 1 and 2. Preferably the polyacrylates are present in the solution of the strong base (solution 2).

The concentration of the polyacrylates in the solutions 1 and/or 2 prepared in process step a) is preferably in the range from 0.1 to 20 g/l, particularly preferably in the range from 0.5 to 10 g/l, further preferably in the range from 1 to 8 g/l and in particular in the range from 4 to 6 g/l. The polyacrylates are of course preferably chosen so that their solubility in water at the desired temperature permits the aforementioned concentrations to be established.

The molecular weight $M_w$ of the polyacrylates used in the process according to the invention is generally in the range from 800 to 250 000 g/mol, preferably in the range from 1000 to 100 000 g/mol, particularly preferably in the range from 1000 to 20 000 g/mol and in particular in the range from 1000 to 10 000 g/mol. In one particularly preferred embodiment of the invention, the molecular weight $M_w$ of the polyacrylates used in the process according to the invention is in the range from 1000 to 5000 g/mol.

b) Mixing and Precipitation

A preferred embodiment of the process according to the invention is one in which the precipitation of the zinc oxide takes place in the presence of a polyacrylate which is obtained from pure acrylic acid. In a particularly preferred embodiment of the invention, Sokalan®PA 15 (BASF Aktiengesellschaft), the sodium salt of a polyacrylic acid, is used.

Step b) comprises the mixing of solutions 1 and 2. The mixing of the two solutions 1 and 2 (aqueous zinc salt solution and aqueous base solution) in process step b) preferably takes place at a temperature in the range from 40° C. to 80° C., further preferably in the range from 50° C. to 70° C., particularly preferably in the range from 55° C. to 65° C. and especially in the range from 58° C. to 62° C.

It is therefore advantageous if the two solutions 1 and 2 are already adjusted to temperatures within these ranges prior to the mixing.

Depending on the zinc salt used, the mixing can be carried out at a pH in the range from 3 to 13. Preferably, the pH during mixing is in the range from 7 to 13, further preferably in the range from 8 to 12.

The mixing in process step b) can take place, for example, by combining an aqueous solution of one or more of the aforementioned zinc salts (solution 1) with an aqueous solution of a mixture of at least one polyacrylate and at least one alkali metal hydroxide or ammonium hydroxide, in particular sodium hydroxide (solution 2).

Alternatively, an aqueous solution of a mixture of at least one polyacrylate and at least one zinc salt (solution 1) can also be combined with an aqueous solution of at least one alkali metal hydroxide or ammonium hydroxide, in particular of sodium hydroxide (solution 2).

Furthermore, an aqueous solution of a mixture of at least one polyacrylate and at least one zinc salt (solution 1) can also be combined with an aqueous solution of a mixture of at least one polyacrylate and at least one alkali metal hydroxide or ammonium hydroxide, in particular sodium hydroxide (solution 2).

In a preferred embodiment of the invention, the mixing in process step b) takes place through metered addition of an aqueous solution of a mixture of at least one polyacrylate and at least one alkali metal hydroxide or ammonium hydroxide, in particular sodium hydroxide (solution 2), to an aqueous solution of at least one zinc salt (solution 1) or through metered addition of an aqueous solution of at least one alkali metal hydroxide or ammonium hydroxide, in particular sodium hydroxide (solution 2), to an aqueous solution of a mixture of at least one polyacrylate and at least one zinc salt (solution 1).

Particularly preferably, an addition of an aqueous solution of a mixture of at least one polyacrylate and at least one alkali metal hydroxide or ammonium hydroxide, in particular sodium hydroxide (solution 2), to an aqueous solution of at least one zinc salt, for example of zinc chloride or zinc nitrate (solution 1), takes place in process step b). In this connection, it is particularly preferred to initially introduce the solution of the zinc salt (solution 1) in a stirred reactor at least partially, preferably completely, and to add the alkaline solution of the polyacrylate (solution 2) to the initially introduced zinc salt solution with stirring.

In a preferred embodiment of the invention, the temperature of the aqueous solution of the mixture of polyacrylate and alkali metal hydroxide or ammonium hydroxide, in particular sodium hydroxide is in the range from 40 to 80° C., particularly preferably in the range from 50 to 70° C. and in particular in the range from 55 to 65° C., prior to the mixing.

In a preferred embodiment of the invention, the temperature of the aqueous solution of the zinc salt, in particular zinc chloride, is in the range from 40 to 80° C., particularly preferably in the range from 50 to 70° C. and especially in the range from 55 to 65° C., prior to the mixing.

Step b) preferably starts at the earliest when the temperatures of the solutions to be mixed differ by at most 8° C., preferably at most 6° C. and in particular at most 4° C.

In a preferred embodiment of the invention, the process is carried out in a manner whereby process step b) takes place in a reaction space in which the solution 1 of at least one zinc salt with a temperature T1 is initially introduced and the solution 2 of at least one strong base with a temperature T2 is metered in, where at least one of the two solutions 1 or 2, preferably solution 2, further comprises at least one polyacrylate, the temperatures T1 and T2 are in the range from 40 to 80° C., particularly preferably in the range from 50 to 70° C. and in particular in the range from 55 to 65° C. and differ by at most 8° C., preferably at most 6° C., further preferably at most 4° C. and in particular at most 2° C.

If the solution 1 is located in the reactor in which the precipitation of the zinc oxide takes place, then preferably, at the start of step b), solution 2 is added to solution 1. If solution 2 is located in the reactor in which the precipitation of the zinc oxide takes place, then at the start of step b), solution 1 is preferably added to solution 2. It is particularly preferred if solution 1 is located in the reactor in which the precipitation of the zinc oxide takes place, and at the start of step b), solution 2 is added. According to the invention, it is preferred for the solutions to be brought together quickly. The addition of solution 1 to solution 2 or solution 2 to solution 1 preferably takes place in a period of from 0.1 to 60 minutes, preferably from 1 to 30 minutes, particularly preferably from 5 to 15 minutes.

It is further preferred that the reactor contents are agitated before, during or after the metered addition, it being possible for the agitation to take place through shaking, stirring, passing through of gas bubbles or using other customary techniques, with stirring being particularly preferred.

During step b), the surface-modified nanoparticulate particles are formed, which precipitate out of the solution to form an aqueous suspension. Following the complete addition of solution 1 to solution 2 or of solution 2 to solution 1, the mixing is continued, preferably with stirring, preferably for a further time in the range from 10 minutes to 6 hours, particularly preferably for a time in the range from 30 minutes to 4 hours and in particular for a time in the range from 1 hour to 3 hours.

In a particularly preferred embodiment of the process in which the solution of the zinc salt is initially introduced in the stirred precipitation reactor and the alkaline solution of the polyacrylate is metered in, the pH of the resulting mixture shifts from the acidic range to the alkaline range. Preferably, the pH of the resulting mixture at the end of step b) is in the range from 9 to 11.

A preferred embodiment of the process according to the invention is one in which at least one of process steps a) to f) is carried out continuously. In the case of a continuously operated procedure, process step b) is preferably carried out in a tubular reactor.

In another embodiment of the invention, the process is carried out continuously in a manner such that process step b) takes place in a first reaction space at a temperature T1, in which an aqueous solution 1 of at least one zinc salt and an aqueous solution 2 of at least one strong base are continuously fed, where at least one of the two solutions 1 and 2 comprises at least one polyacrylate. From this first reaction space the formed suspension is continuously removed, and is transferred to a second reaction space for heating at a temperature T2, during which the surface-modified nanoparticulate particles are formed. As a rule, the continuous process is carried out such that temperature T2 is higher than temperature T1.

c) Concentration

Step c) of the process according to the invention is the concentration of the aqueous suspension of the surface-modified nanoparticulate particles obtained in step b). Within the context of this invention, concentration is understood as meaning the increase in the zinc oxide concentration in the suspension.

In a preferred embodiment of the invention, the suspension obtained in step b) is transferred to another stirred container prior to step c), i.e. process steps b) and c) take place in different reaction spaces.

In a preferred embodiment of the invention, step c) is or comprises a membrane filtration, in particular an ultrafiltration (UF). The method of membrane filtration is known to the person skilled in the art. Membrane filtration is a pressure-driven material separation process based on a sieve effect and dependent primarily on the particle size. Ultrafiltration membranes usually have pore sizes between 1 nm and 100 nm and are thereby able to retain compounds with a molecular weight of from 300 Daltons to 500 000 Daltons (500 kD). The process is therefore typically suitable for retaining biomolecules, bacteria, viruses, polymers, colloidal particles and sugar molecules. Membrane filtration membranes are described inter alia by their nominal molecular weight cutoff (MWCO). The MWCO is normally the smallest molecular weight for which the membrane has a retention of more than 90%, the retention being defined as {1-[(concentration in the permeate)/(concentration in the retentate)]}.

For the process according to the invention, it is particularly important to choose the membrane so that it is as impermeable as possible for zinc oxide and is as permeable as possible for the polyacrylate and the salts present in the resulting suspension, in particular for NaCl.

In many cases, the separation result is not only influenced by the separation limit, but additionally by interactions between membrane and crude solution. For the purposes of the present invention, membranes with a cutoff in the range from 2 to 500 kD, preferably up to 200 kD, can be used. Alternatively, the cutoff can also be quoted in the form of the pore size of the membrane pores. For the purposes of the present invention, membranes with a pore size in the range from 3 to 200 nanometers can advantageously be used. For the membrane filtration, predominantly asymmetrically structured or compositely produced porous membranes of various organic or inorganic materials, such as polymers (e.g. polysulfones, polypropylene, polyacrylonitrile, cellulose acetate), ceramic (e.g. zirconium oxide, aluminum oxide/titanium dioxide), metal, carbon or combinations thereof are suitable. It must be ensured that the materials are stable at the planned filtration temperature (process temperature PT) and the pH of the suspension and that the cutoff of the membranes is below the diameter of the smallest nanoparticles. For mechanical reasons, the separation layers are generally applied to a mono- or multilayered porous substructure made of the same material as, or else several different materials than, the separation layer.

Examples of possible material combinations are given in table 1 below:

TABLE 1

| Separation layer | Substructure (coarser than separation layer) |
|---|---|
| Metal | Metal |
| Ceramic | Metal, ceramic or carbon |
| Polymer | Polymer, metal, ceramic or ceramic on metal |
| Carbon | Carbon, metal or ceramic |

Ceramic: e.g. $\alpha$-$Al_2O_3$, $ZrO_2$, $TiO_2$, SiC, mixed ceramic materials
Polymer: e.g. PP, PTFE, PVDF, polysulfone, polyether sulfone, polyether ether ketone, polyamide, polyester The membranes can be used in flat, tubular, multichannel element, capillary or spiral-wound geometry, for which appropriate pressurized housings which permit separation between retentate (ZnO-containing) and the permeate (low-ZnO, preferably ZnO-free filtrate), are available. The following membranes, for example, can be used:

TABLE 2

| Manufacturer | Membrane | Separation limit (kD) Pore diameter (nm) | |
|---|---|---|---|
| Atech innovations GmbH | UF/TiO$_2$ on α-Al$_2$O$_3$/[1,2] | 20 | kD |
| | UF/TiO$_2$ on α-Al$_2$O$_3$/[1,2] | 50 | nm |
| | MF/α-Al$_2$O$_3$ on α-Al$_2$O$_3$/[1,2] | 0.1; 0.2 | μm |
| Rhodia/Orelis | UF/ZrO$_2$—TiO$_2$ on carbon/[1] | 50; 150; 300 | kD |
| | MF/ZrO$_2$—TiO$_2$ on carbon/[1] | 0.14 | μm |
| Graver Technologies | UF/TiO$_2$ on steel/[1] | 100 | nm |
| GKN Sinter Metals | MF/metal on metal | 0.1-0.3 | μm |
| Microdyn NADIR GmbH | UF/polyether sulfone or polysulfone/[3] | 10-150 | kD |
| Berghoff GmbH | UF/PVDF/[1] | 30 | nm |
| | UF/polyether sulfone/[1] | 100 | kD |
| GE-Osmonics | UF/polysulfone/[3] | 40 | nm |
| | UF/PVDF/[3] | 10 | kD |
| | MF/PVDF/[3] | 300 | nm |
| CUT Membrane Technology | MF/polypropylene/[1] | 200 | nm |
| | UF/polypropylene/[1] | 150 | kD |
| Pall Schumacher | UF/TiO$_2$ or ZrO$_2$ on ceramic/[1,2] | 5.10 and 50 | nm |
| | MF/α-Al$_2$O$_3$ on ceramic | 100 and 200 | nm |

[1]Tubular membrane;
[2]multichannel element;
[3]flat membrane for spiral-wound, bag, disk-stack or specialty modules with mobile membrane and/or stirring units between the membranes
UF: Ultrafiltration
MF: Microfiltration In a preferred embodiment of the invention, the applied pressure on the retentate side is greater than on the permeate side and the pressure difference between retentate side and permeate side, also referred to as transmembrane pressure (TMP), is preferably from 0.2 to 10 bar, particularly preferably 0.4 to 6, bar and in particular 0.5 to 3 bar. In this connection, whenever two or more modules are connected in series, the transmembrane pressure for each module can be lowered by raising the permeate pressure and thus be adapted.

In order to avoid the buildup of a troublesome covering layer of zinc oxide on the membrane surface, which leads to a significant decrease in permeate flow, a relative velocity between membrane and suspension between 0.5-25 m/s is generated by circulatory pumping, mechanical agitation of the membrane or stirring units between the membranes. A further option of preventing the buildup of a covering layer or of breaking down covering layers which have built up is so-called back-flushing, i.e. the reversal of the flow direction through the membrane. Such a reversal is achieved by reversing the pressure ratios, i.e. by applying the higher pressure on the hitherto permeate side and the lower pressure on the retentate side.

The operating temperature (process temperature) is dependent on the membrane stability and the temperature stability of the synthesis solution. Higher temperatures generally lead to higher permeate flows. The operating temperature can be 20° C. to 100° C., it being more advantageous for polymer membranes to maintain a temperature in the range from 20 to 70° C. In the course of the process according to the invention, the process temperature is preferably in the range from 30 to 70° C., particularly preferably in the range from 40 to 60° C.

For the purposes of the process according to the invention, the membranes can be arranged, for example, in disk, spiral-wound, tubular, capillary or hollow-fiber modules. The permeate flows which can be achieved are heavily dependent on the type of membrane and membrane geometry used, on the processing conditions, on the feed composition, i.e. essentially the ZnO concentration and the pH. The flows are typically between 50 and 500 kg/(m$^2$*h).

Table 3 shows typical and preferred values for the individual parameters for membrane filtrations:

TABLE 3

| Parameter | Range | Preferred range |
|---|---|---|
| Transmembrane pressure | 0.2-10 bar | 0.5-3 bar |
| Membrane overflow tubular module | 0.5-8 m/s | 2-5 m/s |
| Membrane overflow flat module | 0.5-8 m/s | 2-5 m/s |
| Membrane overflow rotational module | 2-25 m/s | 5-20 m/s |

The process can take place discontinuously in batch procedures by passing the suspension repeatedly through the membrane modules, or continuously by passing it once through one or more successively connected feed and bleed stages.

In a preferred embodiment of the invention, the concentration is carried out as a fed-batch process.

In a preferred embodiment of the invention, the zinc oxide concentration of the suspension obtained in step b) of zinc oxide particles in step c) is increased through membrane filtration to a value in the range from 5 to 40% by weight, particularly preferably from 10 to 30% by weight and in particular 15 to 25% by weight of zinc oxide. The concentration factors MK can be calculated from the starting concentration and the desired end concentration.

The zinc oxide concentration can be determined by any method known to the person skilled in the art. It is preferred to determine the zinc oxide concentration by elemental analysis.

In step c), not only is the zinc oxide concentration in the suspension increased, but the absolute amount of the dissolved constituents is also lowered. In particular, the absolute amounts of dissolved NaCl and polyacrylate are lowered. Since the zinc oxide remains entirely in the retentate, the depletion of the dissolved constituents, in particular of the NaCl, is essentially dependent on the starting and end concentrations of the zinc oxide.

Apart from being dependent on the starting and end concentrations of the zinc oxide, the extent of depletion of the free polyacrylate, i.e. of the polyacrylate not adsorbed to zinc oxide, is also considerably dependent on the pH of the suspension. High pH values and high salt concentrations shift the sorption equilibrium between polyacrylate adsorbed on the surface of the zinc oxide particles and nonadsorbed, i.e. free, polyacrylate in favor of the free and therefore separable polyacrylate. Polyacrylate adsorbed by zinc oxide is essentially not separated off by the membrane filtration.

According to the invention, for the preparation process, on account of the risk of aggregate formation during drying, it is disadvantageous if the amount of nonadsorbed polyacrylate exceeds a certain amount, measured as content of organic carbon, and if the amount of salt in the suspension exceeds a certain amount, measured as salt content based on the zinc oxide.

According to the invention, it is advantageous for the resulting suspensions if the amount of zinc oxide in the permeate is as low as possible.

If the resulting suspensions are to be passed to a drying, it is advantageous if the amounts of free, i.e. nonadsorbed polyacrylate and salt are as low as possible.

This low polyacrylate loading is preferably achieved by establishing a certain pH.

The pH of the suspension of zinc oxide particles obtained in step b) and to be passed to step c) is in a range from 9 to 14.

The temperature of the suspension obtained in step b) and to be passed to step c) is in a range from 30 to 80° C.

According to the invention, the pH of the suspension of zinc oxide particles obtained in step b) and to be passed to step c) at a processing temperature of from 35 to 45° C., preferably about 40° C., is advantageously adjusted to a value in the range from 10 to 13, further preferably from 11.5 to 12.7 and particularly preferably to a value of from 11.7 to 12.5.

If the processing temperature is in the range from 55 to 65° C., preferably about 60° C., then the pH is preferably adjusted to a value in the range from 9.8 to 13, further preferably from 10.8 to 12.5, yet further preferably from 11.5 to 12.2 and particularly preferably to a value of about 11.9.

In this connection, it is to be noted that the pH is dependent on the respective temperature, i.e. despite the same concentration of the base used, the pH value may change with the temperature.

Aforementioned pH values correspond approximately to NaOH concentrations of from 0.005 to 5.0, preferably from 0.05 to 2.0, particularly preferably from 0.1 to 1.0% by weight, in each case based on the suspension.

Higher pH values lead to the undesired effect that zinc oxide will be dissolved, for example as $Na_2Zn(OH)_4$.

Step c) is thus generally carried out at a temperature (processing temperature) in the range from 20° C. to 80° C., preferably in the range from 30° C. to 70° C., particularly preferably in the range from 35° C. to 65° C. and in particular in the range from 40° C. to 60° C.

In general, the pH of the suspension at the start and at the end of step c) is essentially the same, provided that step c) comprises no evaporation of water. The evaporation of water leads to an increase in the concentration of hydroxyl ions and thus to an increase in the pH.

In a further embodiment of the invention, the zinc oxide concentration of the suspension obtained after step b) is increased merely by evaporating water or by evaporating water in addition to the previously described membrane filtration. Methods of evaporating water are known to the person skilled in the art. In one embodiment of the invention, the water is evaporated under reduced pressure at simultaneously elevated temperature. In a preferred embodiment of the invention, the zinc oxide concentration of the suspension of zinc oxide particles obtained in step b) is adjusted in step c) to a value in the range from 10 to 70% by weight, particularly preferably from 20 to 65% by weight and in particular 30 to 60% by weight of zinc oxide.

d) Purification

The process according to the invention preferably comprises a step d). Step d) of the process according to the invention is the further purification of the concentrated aqueous suspension of the surface-modified nanoparticulate zinc oxide particles obtained in step c). This purification comprises the further separation of the salts, in particular of NaCl, and of the polyacrylate not adsorbed to the zinc oxide particles. This separation takes place, like step c), preferably with the help of a membrane separation process. Particularly preferably, step d) is or comprises a diafiltration. Diafiltration is a special case of membrane filtration in which the amount of liquid phase of the permeate obtained by filtration, in which salts and free polyacrylate are located, is replaced continuously or stepwise by approximately the same amount of liquid phase.

According to the invention, the suspensions are therefore preferably firstly concentrated in step c) by a membrane filtration and then are largely freed from salts and from nonadsorbed (free) polyacrylate by a diafiltration in step d).

Steps c) and d) can be carried out in the same apparatus or in different apparatus, the so-called separation modules. The techniques of diafiltration per se are known to the person skilled in the art.

The extent of the removal of the salts, in particular of NaCl, can be adjusted through the suitable choice of concentration factor MK and diafiltration coefficient MA. In this connection, the concentration factor MK is the quotient of zinc oxide content in the suspension after and before the concentration and the diafiltration coefficient MA is the quotient of separated-off amount of permeate and amount of retentate.

The amount of polyacrylate present overall is dependent, inter alia, on the pH during steps c) (concentration) and d) (diafiltration) and on the salt concentration. High pH values and high salt concentrations shift the sorption equilibrium between polyacrylate adsorbed by ZnO and free polyacrylate in favor of the free and thus separable polyacrylate. Polyacrylate adsorbed by ZnO is essentially not separated off by the membrane filtration.

In one embodiment of the invention, the diafiltration of step d) is carried out with water. Water which can be used is local drinking water, which is preferably present in softened form, or demineralized water.

In a preferred embodiment of the invention, the diafiltration of step d) is carried out with at least two different liquid phases.

In one embodiment of the invention, the exchange phase used is completely demineralized water. In a further embodiment of the invention, the exchange phase used is drinking water which corresponds to the particular local drinking water ordinance. The liquid phase is particularly preferably water, preferably drinking water, which has the lowest possible content of divalent cations such as magnesium and calcium ions. In one embodiment of the invention, drinking water is subjected prior to its use in the process according to the invention to a customary method for depleting such divalent ions (softening). The salt content of the exchange phase naturally determines the lowest possible salt content of the liquid phase of the retentate.

It is a particularly preferred embodiment of the invention to subject the concentrated zinc oxide suspension obtained in step c) initially to a first diafiltration with an alkaline solution (hydroxide solution), preferably sodium hydroxide solution, as a first liquid phase and then to a second diafiltration with water as second liquid phase. Irrespective of how many diafiltrations are carried out, it is particularly preferred to carry out the last diafiltration with water.

If step c) does not comprise an evaporation of water, the pH of the concentrated suspension of zinc oxide particles obtained in step c) and to be conveyed to step d) is approximately equal to the pH of the suspension fed to step c) (see above under concentration (step c)).

Higher pH values lead to the undesired effect that zinc oxide passes into solution, for example as $Na_2Zn(OH)_4$.

The purification is preferably carried out under identical or at least similar conditions (temperature, pressure, pH) to the concentration.

The diafiltration with the alkaline solution is preferably carried out such that the alkaline solution has the same pH as the suspension to be filtered. A diafiltration with water of neutral pH leads to a lowering of the pH of the filtered suspension.

The diafiltration with water following the diafiltration with the alkaline solution leads to the diafiltered zinc oxide suspension obtained therefrom having, at a temperature in the range from 40° C. to 60° C., a pH in the range from 8 to 13, particularly preferably 9 to 12, in particular in the range from 9.5 to 11.5 and most preferably in the range from 10 to 11.

At a processing temperature of about 40° C., the pH of the suspension obtained at the end of step d) is preferably in the range from 9.6 to 12.0, further preferably in the range from 10.0 to 11.6 and particularly preferably in the range from 10.4 to 11.2.

At a processing temperature of about 60° C., the pH of the suspension obtained at the end of step d) is preferably in the range from 9.2 to 11.6, further preferably in the range from 9.6 to 11.2 and particularly preferably in the range from 10.0 to 10.8.

The lowering of the pH to values in these ranges leads to the equilibrium between adsorbed polyacrylate and nonadsorbed ("free") polyacrylate being shifted in favor of the adsorbed polyacrylate.

According to the invention, it is preferred to shift the equilibrium in favor of the adsorbed polyacrylate.

The purified concentrated suspension produced in step d) is preferably collected in a stirred storage container.

The extent of the depletion of the zinc oxide suspension from the undesired salts such as, for example, NaCl is dependent on the zinc oxide concentration and on the diafiltration coefficient MA. MA is the quotient $$MA = \frac{\text{mass of separated} - \text{off permeate}}{\text{mass of retentate}}$$

Preferably, MA is at least 3, further preferably at least 4, particularly preferably at least 5.

The amount of NaCl in the zinc oxide suspension is reduced during step d), based on the amount of NaCl in the zinc oxide suspension at the end of step c), preferably by at least 90%, further preferably by at least 95% and particularly preferably by at least 99%. In particular, the amount of NaCl is reduced by at least 99.5%.

In one embodiment of the invention, the amount of NaCl still present in the suspension is preferably in the range from 2.0 to 0.005, further preferably in the range from 1.0 to 0.01 and particularly preferably in the range from 0.5 to 0.05 gram of NaCl per 100 grams of zinc oxide.

If the liquid exchange phase has a pH in the range from 6 to 11, preferably from 7 to 10, then the depletion of polyacrylate is lower than at pH values of greater than 11.

According to the invention, it is preferred to adjust the polyacrylate loading of the zinc oxide particles, expressed by the quotient $$\text{Polyacrylate loading} = \frac{\text{mass of organic carbon}}{\text{mass of zinc oxide}}$$

to a value in the range from 0.2% to 1%.

At the end of step d), the amount of organic carbon, which is a measure of the amount of polyacrylate in the suspension, is preferably in the range from 2.0 to 0.01, further preferably in the range from 1.0 to 0.05 and particularly preferably in the range from 0.7 to 0.1 gram per 100 grams of zinc oxide.

e) Drying

Preferably, the process according to the invention comprises a step e). Step e) of the process according to the invention is the drying of the surface-modified nanoparticulate particles obtained in step d). In principle, in step e), all of the known techniques for drying can be used. Preferably, step e) is or comprises a spray-drying.

Spray-drying belongs to the class of convective drying. The energy required to vaporize the liquid phase is supplied to the material via the drying gas used. The spraying of the product brings about an increase in the heat-transfer and mass-transfer interface and therefore an increase in the rate of the drying process. The zinc oxide particles present in suspension are sprayed at the upper end of a wide cylindrical container through nozzles or by means of a rapidly rotating atomizer disk to give a fine mist, with spraying through nozzles being preferred.

The spraying rate is preferably 10 to 1000 kg per hour, further preferably 100 to 500 kg per hour, particularly preferably 150 to 400 kg per hour. Preferably, the atomization is achieved through a two-material nozzle. Alternatively, the atomization in the process according to the invention can likewise be constituted via other nozzle types, comprising pressurized nozzles, electrostatic atomizers, ultrasound atomizers and multi-material nozzles.

Hot, preferably filtered air or an inert gas is introduced into the spray cone, preferably from above countercurrently or cocurrently to the spray cone, but if appropriate also countercurrently or cocurrently from below or from the side. The drying gas preferably has a temperature in the range from 100 to 650° C., particularly preferably from 160 to 300° C.

The large, relative surface of the liquid droplets brings about an effective and rapid exchange of heat and mass between the two phases. The zinc oxide drops down as fine powder and is preferably discharged at the bottom of the dryer with the gas stream. The gas-conveyed particles can be obtained through dust filters, electrofilters or centrifugal separators (cyclones), preferably through dust filters, particularly preferably through dust filters with coated fabric hoses.

In a preferred embodiment of the invention, the introduction rate of gas and heat is such that it corresponds to the evaporation rate of the water from the droplets. According to the invention, the suspension of zinc oxide particles obtained from step d) is preferably conveyed to the spray tower via pumps and sprayed via nozzles located in the top of the tower. The introduced drying air with a temperature in the range from preferably 160 to 350° C. evaporates the adhering water, such that the zinc oxide is obtained as a fine dry powder at the outlet of the tower (outlet temperature 50 to 160° C.).

Preferably, a large temperature difference between inlet and outlet temperature should be chosen, in particular inlet temperatures of 200-350° C. and outlet temperatures of 50-90° C. Via this, it is possible to adjust the residual moisture of the product. This is preferably determined using a thermogravimetric measurement method (30 minutes at 200° C.). At the end of step e), the zinc oxide preferably has a water content of less than 5, preferably of less than 2, particularly preferably of less than 1% by weight. Step e) is preferably carried out continuously.

f) Thermal Aftertreatment

Preferably, the process according to the invention further comprises a step f). Step f) is the thermal aftertreatment of the dried, surface-modified nanoparticulate zinc oxide particles preferably obtained in step e). The dry product preferably obtained in step e) is preferably subjected to a high-temperature treatment. The thermal aftertreatment preferably is or comprises a heating of the zinc oxide particles preferably obtained in step e) to temperatures in the range from 150° C. to 250° C., preferably from 180° C. to 230° C. and in particular from 200° C. to 220° C.

According to the invention, this heating takes place during a time in the range from 0.5 to 10 hours, preferably from 1 to 6 hours and in particular from 2 to 4 hours. If a higher temperature is chosen for the aftertreatment, the chosen duration of the treatment can be shorter. Thus, for example, an aftertreatment for about 4 hours at 180° C. leads to approximately the same optical properties of the zinc oxide particles as an aftertreatment for approximately 2 hours at 200° C. Longer times and/or higher temperatures than those described previously can of course likewise be used, but do not necessarily lead to significant improvements in the product.

The heating can be carried out under reduced pressure and/or in the presence of inert gas, such as, for example, nitrogen.

In the process according to the invention, step f) can be carried out either continuously or discontinuously, i.e. the spray-dried product obtained in step e) is subjected to step f) in portions. The entire spray-dried process product obtained in step e) can of course also be subjected to step f) in one portion.

After step f), the process product is cooled to a temperature in the range from 0° C. to 100° C., preferably from 10° C. to 70° C. and in particular from 20° C. to 60° C.

Preferably, prior to packaging, the prepared product is divided into batches and these are thoroughly mixed to give a homogeneous, uniform product. This division into batches can preferably be achieved by carrying out step f) discontinuously or via a downstream container. This container particularly preferably comprises a stirrer.

g) Grinding

Preferably, the process according to the invention further comprises a step g). Preferably, step g) follows optional step f) and comprises a grinding of the zinc oxide obtained preferably in step f). This grinding is preferably jet grinding. Jet grinding is a type of impact grinding in which the grinding material is accelerated in a rapid stream of gas and is comminuted through impaction of the particles with one another or against an impaction wall. The grinding effect depends here decisively on the impact speed and/or impact energy. According to the invention, the gas pressure is preferably in the range from 5 to 20, preferably from 7 to 15 bar.

The invention is based on the finding that, by virtue of a surface modification of nanoparticulate zinc oxide with polyacrylates, it is possible to achieve a long-term stability of suspensions of the surface-modified nanoparticulate zinc oxide, in particular in cosmetic preparations, without undesired changes in the pH during storage of these preparations.

An advantageous embodiment of the process according to the invention is one in which the surface-modified nanoparticulate zinc oxide particles have a high light transmission in the region of visible light (VIS) and a low light transmission in the region of near ultraviolet light (UV-A). Preferably, the ratio of the logarithm of the percentage transmission (T) at a wavelength of 360 nm and the logarithm of the percentage transmission at a wavelength of 400 nm [$\ln T_{360\,nm}/\ln T_{450\,nm}$] is at least 7, preferably at least 10 and in particular at least 13.

A further advantageous embodiment of the process according to the invention is one in which the surface-modified nanoparticulate zinc oxide particles obtainable by the process according to the invention preferably have a BET surface area in the range from 15 to 200 m$^2$/g, preferably 20 to 100 m$^2$/g, particularly preferably 30 to 50 m$^2$/g.

According to a particularly preferred embodiment of the present invention, the surface-modified nanoparticulate zinc oxide particles have a diameter of from 20 to 200 nm, preferably 20 to 100 nm. This size range is particularly advantageous since, for example following redispersion of such zinc oxide particles, the resulting suspensions are transparent and thus do not influence the coloration upon addition to cosmetic formulations. Moreover, this also gives rise to the possibility of use in transparent films.

The present invention further provides the surface-modified nanoparticulate zinc oxide particles obtainable by the process according to the invention.

The present invention further provides the use of the surface-modified nanoparticulate zinc oxide particles obtainable by the process according to the invention as UV protectants in cosmetic sunscreen preparations, as stabilizers in plastics and as antimicrobial active ingredients.

According to a preferred embodiment of the present invention, the surface-modified nanoparticulate zinc oxide particles are redispersible in liquid media and form stable suspensions. This is particularly advantageous, for example, since the suspensions do not have to be dispersed again prior to further processing, but can be processed directly.

According to a preferred embodiment of the present invention, the surface-modified nanoparticulate zinc oxide particles are redispersible in polar organic solvents, where they form stable suspensions. This is particularly advantageous since, as a result of this, uniform incorporation for example into plastics or films is possible.

According to a further preferred embodiment of the present invention, the surface-modified nanoparticulate zinc oxide particles are redispersible in water, where they form stable suspensions. This is particularly advantageous since this opens up the possibility of using the zinc oxide obtainable according to the invention for example in cosmetic formulations, where dispensing with organic solvents may represent a major advantage. Also conceivable are zinc oxide suspension in mixtures of water and polar organic solvents.

The present invention further provides aqueous suspension of zinc oxide particles obtainable by the process according to the invention. These suspensions are obtained, for example, by dispersing the zinc oxide particles obtained according to step f).

The present invention further provides aqueous suspension of surface-modified nanoparticulate zinc oxide particles, where these suspensions are obtainable by steps a) to c) or a) to d) of the process according to the invention. This may be advantageous in certain cases since the working steps purification, drying, grinding and thermal aftertreatment can be dispensed with.

In one embodiment of the invention, dispersants are added to these suspensions before or during step c) in the range from 0.01 to 5.0% by weight, preferably from 0.1 to 3.0% by weight, based on zinc oxide, in order to further increase the long-term stability. Suitable dispersants are, for example, nonionic molecular or polymeric surfactants or dispersants, such as ethoxylated fatty alcohols, polyethylene glycol-polypropylene glycol block polymers, the properties of which can be adjusted via the size of the polyethylene glycol and/or polypropylene glycol blocks.

Also suitable are ionic molecular and/or polymeric surfactants and/or wetting agents or dispersants which carry, for example, carboxylic acid, sulfonic acid, phosphonic acid groups, quaternary ammonium groups. These include, for example: C12-C18 alkylsulfonic acid and salts thereof, alkylbenzene- and alkylnaphthalenesulfonic acids and salts thereof, e.g. dodecylbenzenesulfonic acid.

Polycarboxylic acids and salts thereof based on at least one α,β-unsaturated carboxylic acid, for example acrylic acid, methacrylic acid, dimethacrylic acid, ethacrylic acid, maleic acid, citraconic acid, methylenemalonic acid, crotonic acid, isocrotonic acid, fumaric acid, mesaconic acid and itaconic acid. Polyacrylates based on acrylic acid, methacrylic acid, maleic acid or mixtures thereof are preferably used. Further suitable copolymerizable compounds are N-vinylcaprolactam, N-vinylimidazole, N-vinyl-2-methylimidazole, N-vinyl-4-methylimidazole, vinyl acetate, vinyl propionate, isobutene or styrene.

Polyvinylphosphonic acids and polymeric amines based on saponified polyvinylformamide or ethylenimine are also suitable.

Suitable dispersants are also:

| Dispersant | Average molecular weight | Trade name of BASF SE |
|---|---|---|
| Naphthalenesulfonic acid-formaldehyde condensate Na salt | 20 kD | Tamol ®NH 7519 |
| Maleic acid-olefin copolymer Na salt | 12 kD | Sokalan ® CP 9 |
| Modified polyacrylic acid Na salt | 4 kD | Sokalan ® CP 10 |
| Block copolymer (10% PEG): PEG-PPG-PEG | 2 kD | Pluronic ® 6100 |
| Block copolymer (50% PEG): PEG-PPG-PEG | 6.5 kD | Pluronic ® 10500 |
| Block copolymer (80% PEG): PEG-PPG-PEG | 8 kD | Pluronic ® 6800 |

Preferred dispersants are the polyacrylates described above, with polyacrylates of the Sokalan® (BASF) brand being particularly preferred. Polyacrylates of the brands Sokalan®PA such as, for example, Sokalan®PA 15, and Sokalan®CP such as, for example, Sokalan®CP 9 are especially suitable.

The invention further provides the use of the above-described aqueous suspensions of the surface-modified nanoparticulate zinc oxide particles according to the invention as UV protectants in cosmetic sunscreen preparations, as stabilizers in plastics and as antimicrobial active ingredients.

EXAMPLES

The invention will be explained in more detail by reference to the examples below.

Step a): Preparation of Solutions 1 and 2

Preparation of a solution of water and at least one zinc salt (solution 1):

480 kg of aqueous $ZnCl_2$ solution with a concentration of 0.4 mol of $ZnCl_2$ per kg of solution were prepared in the reaction container in which the mixing was also subsequently carried out. For this, 439.75 kg of completely demineralized water were metered into the container at room temperature and 40.25 kg of $ZnCl_2$ (65% strength by weight aqueous solution) were added. The temperature in the container was adjusted to about 60° C., the pH in the container was adjusted to about 4.5 by adding 30% strength by weight hydrochloric acid.

Preparation of a solution of water and at least one strong base which moreover also comprises at least one polyacrylate (solution 2):

The mixture of 496 kg of sodium hydroxide solution with a concentration of 0.8 mol of NaOH per kg of solution and 4 g of Sokalan®PA15 per kg of solution was prepared as follows: 428.10 kg of demineralized water were metered into the container. 4400 g of Sokalan®PA15 (45% strength by weight aqueous solution) and 63.5 kg of 25% strength by weight NaOH were weighed into this. The temperature of this alkaline solution was adjusted to 60° C.

Step b): Mixing Solutions 1 and 2 Prepared in Step a) (Precipitation)

The addition of solution 2 to solution 1 was started when both solutions had reached a temperature of 60° C. with a tolerance of +/−2.0° C. Solution 2 was added to solution 1 uniformly with stirring over ca. 5 minutes. The speed of the stirrer was ca. 100 $min^{-1}$ (energy input ca. 0.7 W/l). The resulting mixture was stirred for a further 2 hours.

Analysis of Sorption Equilibrium and ZnO Solubility

Synthesis product with 1.6% by weight of ZnO, 2.5% by weight of NaCl and 0.2% by weight of Na polyacrylate was ultrafiltered at 60° C. with recycling of the permeate and admixed portionwise with sodium hydroxide solution. Every 30 minutes after the respective addition of sodium hydroxide solution, a sample was taken to determine the individual values.

Table 4 shows the dependency of the sorption equilibrium of the polyacrylate and of the zinc oxide going into solution on the respective pH.

The pH range is preferably one in which the amount of free, i.e. nonadsorbed, polyacrylate in the permeate is as high as possible and the zinc content (dissolved zinc salt) of the permeate is simultaneously as low as possible.

Accordingly, at a processing temperature in the range from 40 to 60° C., a pH in the range from 11.0 to 12.0, in particular from 11.5 to 11.8, is particularly preferred. The adsorbed polyacrylate can be calculated as the difference (polyacrylate in the retentate) minus (polyacrylate in the permeate).

The measurement parameter used for the particular polyacrylate content is preferably the elemental analytical determination of the carbon content of retentate and permeate.

Step c): Concentration by Membrane Filtration (Ultrafiltration)

Figure 1:
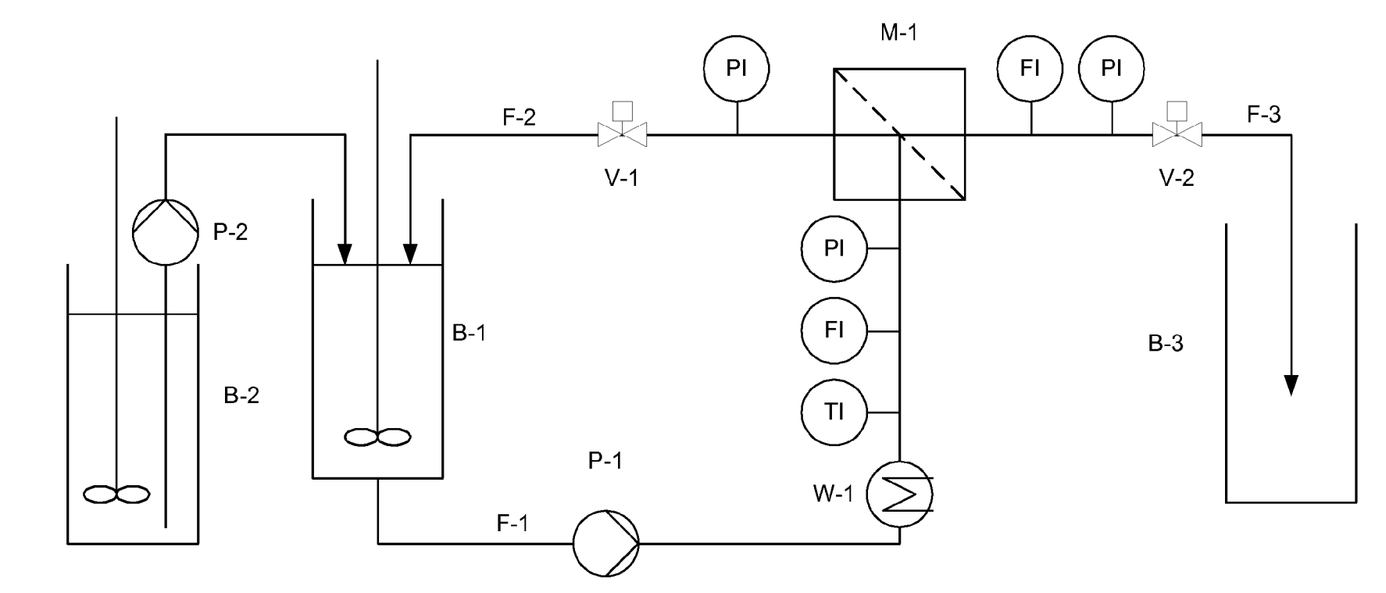

Concentration by membrane filtration is shown diagrammatically in FIG. 1. The apparatus consisted of a pump cycle which comprised a storage vessel B-1, a pump P-1, a heat exchanger W-1, a membrane module M-1 and a pressure relief valve V-1. Upstream of the membrane module, a flow measurement Fl, a temperature measurement TI and a pressure measurement PI (feed=F-1) were integrated, as well as a further pressure measurement PI after the module (retentate=F-2). The pressure in the permeate discharge F-3 could be adjusted via a pressure relief valve V-2 and a pressure measurement PI. The permeate flow was measured using a flow meter Fl in the permeate discharge and the separated-off amount of permeate in the collecting vessel B-3 was determined using a balance.

The module was fitted with a polypropylene tubular membrane from CUT Membrane Technology (external diameter=7 mm, internal diameter=5.5 mm, length=1000 mm) with a separation limit of 150 kD. The flow rate of the suspension in the membrane tube was regulated to 4 m/s, the transmembrane pressure (TMP=arithmetic mean of the pressures at the module entry and module exit, reduced by the permeate pressure) was regulated to 1 bar and the temperature was regulated to 60° C.

At the start of the experiment, the cycle was filled with the ZnO synthesis suspension (1.6% ZnO, 2.5% NaCl, 0.2% sodium polyacrylate Sokalan® PA 15), the plant was set in operation and the pH was raised by adding 5 g of NaOH per kg of suspension. Subsequently, filtrate was drawn off and further ZnO synthesis discharge (likewise admixed with 5 g of NaOH per kg of suspension) was then fed from the container B-2 according to the amount of separated-off ZnO-free permeate using a pump P-2. After reaching the desired ZnO concentration of ca. 20% by weight, the diafiltration was started. For this, filtrate was drawn off and the diafiltration medium was then fed from the container B-2 according to the amount of separated-off ZnO-free permeate using the pump P-2 until the pregiven MA value was reached.

Step d) Depletion of Undesired Constituents in the Suspension

Table 5 shows the dependency of the NaCl depletion on the diafiltration coefficient MA and the stationary ZnO concentration:

TABLE 5

| | Relative NaCl depletion (%) | | |
|---|---|---|---|
| MA | 10% by wt. ZnO | 20% by wt. ZnO | 30% by wt. ZnO |
| 0 | 0.00 | 0.00 | 0.00 |
| 1 | 67.08 | 71.35 | 76.04 |
| 2 | 89.16 | 91.79 | 94.26 |
| 3 | 96.43 | 97.65 | 98.62 |
| 4 | 98.83 | 99.33 | 99.67 |
| 5 | 99.61 | 99.81 | 99.92 |
| 6 | 99.87 | 99.95 | 99.98 |

Decreasing the pH shifts the equilibrium between free polyacrylate and polyacrylate adsorbed to the zinc oxide surface in favor of the adsorbed polyacrylate.

If step d) is carried out with water, then the depletion of polyacrylate is lower since essentially the NaOH content and thus the pH decrease.

Table 6 shows the course of the depletion of NaCl and free polyacrylate in the retentate during concentration and diafiltration.

Up to MA=3, NaCl was depleted by 99.9% and the organic carbon by 91.2%, in each case based on zinc oxide. The pH measured at processing temperature PT (40° C.) dropped from 12.4 to 10.8. Above MA=3, depletions and pH no longer changed within the scope of measurement accuracy, merely the ion-sensitive conductivity in the permeate dropped further with increasing MA.

Table 7 shows the influence of the pH on the acrylate depletion.

Step e)

The concentrated and purified suspension obtained from step d) was metered into a spray dryer at ambient temperature for the drying via a volumetric pump with a mass stream of 40.0 kg/h. In this, it was atomized overhead using a two-material nozzle with a ratio atomization gas: dispersion=1:1 Nm³/kg (normal cubic meters per kilogram). Drying gas with a temperature of 130-350° C. was fed axially into the spray tower in a cocurrent manner, an exit temperature at the spray tower exit of 50-150° C. being adjusted via the amount of gas.

The dry product thus obtained was separated off in a filter and collected.

Step f)

The dry material from step e) was introduced into a contact drying apparatus and heated. The temperature of the product bed was measured using a thermocouple and a product temperature of 80-240° C. was retained over a period of from 1 to 8 hours (see table 8). Zinc oxide particles which had been aftertreated at temperatures in the range from 180-220° C. exhibited the best optical properties. Aftertreatments at temperatures above 240° C. or below 160° C. led to comparatively somewhat poorer optical properties. The duration of the thermal aftertreatment likewise has an influence on the optical properties, where a longer aftertreatment duration improves the optical properties, but beyond a certain timepoint no further significant improvement occurs. Thus, aftertreatments for more than 4 hours at 180° C. or more than 2 hours at 200° C. no longer led to further improvements (tables 8 and 9).

TABLE 8

Kinetics of the shift in the adsorption edge during thermal aftertreatment at 200° C.

| Time [h] | Wavelength of minimal transmission [nm] | Transmission at 360 nm [%] | Transmission at 450 nm [%] |
|---|---|---|---|
| 0 | 348 | 23.2 | 87.8 |
| 0.25 | 354 | 14.6 | 88.5 |
| 0.5 | 356 | 14.7 | 88.8 |
| 1 | 356 | 12.4 | 88.3 |
| 2 | 358 | 13.0 | 88.8 |
| 4 | 358 | 11.9 | 88.1 |
| 8 | 358 | 11.4 | 89.9 |
| 24 | 358 | 13.2 | 88.7 |

TABLE 9

Kinetics of the shift in the adsorption edge during thermal aftertreatment at 180° C.

| Time [h] | Wavelength of minimal transmission [nm] | Transmission at 360 nm [%] | Transmission at 450 nm [%] |
|---|---|---|---|
| 0 | 348 | 33.0 | 91.4 |
| 1 | | | |
| 2 | 356 | 26.8 | 92.6 |
| 4 | 356 | 32.9 | 93.5 |
| 6 | 358 | 26.7 | 92.3 |
| 8 | 358 | 29.9 | 92.8 |
| 9 | 358 | 26.3 | 92.3 |
| 24 | 358 | 29.2 | 93.2 |

Step g)

The product thermally aftertreated in step f) was subjected to a comminution in a further process step g). Here, the product was fed with a mass stream of 4 kg/h to a jet mill together with a gas stream which was generated by the decompression of 8 bar of compressed air, and comminuted as a result of the particles colliding with one another and as a result of the particles contacting with the walls of the mill, which leads to a reduction in the Sauter diameter (SMD). This was reduced in experiments from SMD=5-10 µm (after step f) to SMD=1-3 µm after step g), e.g. from 5.8 µm to 1.86 µm.

APPLICATION EXAMPLES

Cosmetic Formulations

General Procedure for Producing Cosmetic Preparations Comprising Zinc Oxide Prepared According to the Invention The respective phases A and C were heated separately to ca. 85° C. Phase C and the zinc oxide were then stirred into phase A with homogenization. Following brief afterhomogenization, the emulsion was cooled to room temperature with stirring and topped up. All quantitative data is based on the total weight of the preparations.

Example 1

Emulsion A, Comprising 3% by Weight of Uvinul® T150 and 4% by Weight of Zinc Oxide Prepared According to the Invention

| Phase | % by wt. | INCI |
|---|---|---|
| A | 8.00 | Dibutyl adipate |
|  | 8.00 | $C_{12}$-$C_{15}$ alkyl benzoate |
|  | 12.00 | Cocoglycerides |
|  | 1.00 | Sodium cetearyl sulfate |
|  | 4.00 | Lauryl glucoside, polyglyceryl-2 |
|  | 2.00 | Cetearyl alcohol |
|  | 3.00 | Ethylhexyl triazone (Uvinul ® T150) |
|  | 1.00 | Tocopheryl acetate |
| B | 4.0 | Zinc oxide |
| C | 3.00 | Glycerin |
|  | 0.20 | Allantoin |
|  | 0.30 | Xanthan gum |
|  | 0.02 | Triethanolamine |
|  | ad 100 | Aqua dem. |

Example 2

Emulsion B, Comprising 3% by Weight of Uvinul® T150, 2% by Weight of Uvinul® A Plus and 4% by Weight of Zinc Oxide Prepared According to the Invention

| Phase | % by wt. | INCI |
|---|---|---|
| A | 8.00 | Dibutyl adipate |
|  | 8.00 | C12-C15 alkyl benzoate |
|  | 12.00 | Cocoglycerides |
|  | 1.00 | Sodium cetearyl sulfate |
|  | 4.00 | Lauryl glucoside, polyglyceryl-2 |
|  | 2.00 | Cetearyl alcohol |
|  | 3.00 | Ethylhexyl triazone (Uvinul ® T150) |
|  | 1.00 | Tocopheryl acetate |
|  | 2.00 | Diethylamino hydroxybenzoyl hexyl benzoate (Uvinul ® A Plus) |
| B | 4.0 | Zinc oxide |
| C | 3.00 | Glycerin |
|  | 0.20 | Allantoin |
|  | 0.30 | Xanthan gum |
|  | 1.50 | Magnesium aluminum silicate |
|  | ad 100 | Aqua dem. |

Example 3

Emulsion A, Comprising 3% by Weight of Uvinul® T150 and 4% by Weight of Zinc Oxide Prepared According to the Invention

| Phase | % by wt. | INCI |
|---|---|---|
| A | 8.00 | Dibutyl adipate |
|  | 8.00 | C12-C15 alkyl benzoate |
|  | 12.00 | Cocoglycerides |
|  | 1.00 | Sodium cetearyl sulfate |
|  | 4.00 | Lauryl glucoside, polyglyceryl-2 |
|  | 2.00 | Cetearyl alcohol |
|  | 3.00 | Ethylhexyl triazone (Uvinul ® T150) |
|  | 1.00 | Tocopheryl acetate |
|  | 2.00 | Diethylamino hydroxybenzoyl hexyl benzoate (Uvinul ® A Plus) |
| B | 4.0 | Zinc oxide |
| C | 3.00 | Glycerin |
|  | 0.20 | Allantoin |
|  | 0.30 | Xanthan gum |
|  | 1.50 | Magnesium aluminum silicate |
|  | ad 100 | Aqua dem. |

Example 4

Emulsion B, Comprising 3% by Weight of Uvinul® T150, 2% by Weight of Uvinul® A Plus and 4% by Weight of Zinc Oxide Prepared According to the Invention

| Phase | % by wt. | INCI |
|---|---|---|
| A | 8.00 | Dibutyl adipate |
|  | 8.00 | $C_{12}$-$C_{15}$ alkyl benzoate |
|  | 12.00 | Cocoglycerides |
|  | 1.00 | Sodium cetearyl sulfate |
|  | 4.00 | Lauryl glucoside, polyglyceryl-2 |
|  | 2.00 | Cetearyl alcohol |
|  | 3.00 | Ethylhexyl triazone (Uvinul ® T150) |
|  | 1.00 | Tocopheryl acetate |
| B | 4.0 | Zinc oxide |
| C | 3.00 | Glycerin |
|  | 0.20 | Allantoin |
|  | 0.30 | Xanthan gum |
|  | 0.02 | Triethanolamine |
|  | ad 100 | Aqua dem. |

Example 5

| Phase | % by wt. | Constituents | INCI |
|---|---|---|---|
| A | 7.50 | Uvinul ®MC 80 | Ethylhexyl methoxycinnamate |
|  | 1.50 | Tween ®20 | Polysorbate-20 |
|  | 3.00 | Pationic ®138 C | Sodium lauroyl lactylate |
|  | 1.00 | Cremophor ®CO 40 | PEG-40 hydrogenated castor oil |
|  | 1.00 | Cetiol ®SB 45 | *Butyrospermum Parkii* (Shea Butter) |
|  | 6.50 | Finsolv ®TN | C12-15 alkyl benzoate |
| B | 5.00 | Zinc oxide | Zinc oxide |
| C | 1.00 | D-Panthenol 50 P | Panthenol, propylene glycol |
|  | 4.00 | 1,2-Propanediol | 1,2-Propanediol |
|  | 0.30 | Keltrol ® | Xanthan gum |
|  | 0.10 | Edeta ®BD | Disodium EDTA |
|  | 2.00 | Urea | Urea |
|  | 2.00 | Simulgel ®NS | Hydroxyethyl acrylate/sodium acryloyldimethyl taurate copolymer, squalane, polysorbate 60 |
|  | 64.10 | Water dem. | Aqua dem. |
| D | 0.50 | Lactic acid | Lactic acid |
|  | 0.50 | Euxyl ®K 300 | Phenoxyethanol, methylparaben, butylparaben, ethylparaben, propylparaben, isobutylparaben |

Phase A was heated to 80° C., then phase B was added, the mixture was homogenized for 3 minutes. Phase C was heated separately to 80° C. and stirred into the mixture of phases A and B. The mixture was then cooled to 40° C. with stirring, then phase D was added. The lotion was briefly afterhomogenized.

Example 6

| Water-in-silicone formulation | | |
|---|---|---|
| % by wt. | Ingredients | INCI |
| Phase A | | |
| 25.0 | Dow Corning 345 Fluid | Cyclopentasiloxane, cyclohexasiloxane |
| 20.0 | Luvitol ™ Lite | Cyclopentasiloxane |
| 8.0 | Uvinul © MC 80 | Ethylhexyl methoxycinnamate |
| 4.0 | Abil © EM 90 | Cetyl PEG/PPG-10/1 dimethicone |
| 7.0 | T-Lite ™ SF | Titanium dioxide (and) aluminum hydroxide (and) dimethicone/methicone copolymer |

-continued

| Water-in-silicone formulation | | |
|---|---|---|
| % by wt. | Ingredients | INCI |
| Phase B | | |
| 17.0 | Ethanol 95% | Alcohol |
| 5.0 | Zinc oxide | Zinc oxide |
| 4.0 | 1,2-Propanediol | 1,2-Propanediol |
| 5.0 | Water dem. | Aqua dem. |
| 3.0 | Glycerol 87% | Glycerin |
| 1.0 | Talc (C/2S, Bassermann) | Talc |

Phases A and B are homogenized at ca. 11 000 rpm for 3 minutes, then B is added to A and homogenized for a further minute.

Example 7

| A (% by wt.) | | |
|---|---|---|
| 7.00 | Uvinul ®MC 80 | Ethylhexyl methoxycinnamate |
| 2.00 | Uvinul ®A Plus | Dimethylamino hydroxybenzoyl hexyl benzoate |
| 5.00 | Uvinul ®N 539 T | Octocrylene |
| 3.00 | Octyl salicylate | Octyl salicylate |
| 3.00 | Homomenthyl salicylate | Homosalate |
| 2.00 | Antaron ®V-216 | PVP/hexadecene copolymer |
| 0.50 | Abil ®350 | Dimethicone |
| 0.10 | Oxynex ®2004 | BHT, ascorbyl palmitate, citric acid, glyceryl stearate, propylene glycol |
| 2.00 | Cetyl alcohol | Cetyl alcohol |
| 2.00 | Amphisol ®K | Potassium cetyl phosphate |
| B | | |
| 3.00 | Zinc oxide | Zinc oxide |
| 5.00 | 1,2-Propylene glycol Care | Propylene glycol |
| 57.62 | Water | Aqua dem. |
| 0.20 | Carbopol ®934 | Carbomer |
| 5.00 | Witconol ®APM | PPG-3 myristyl ether |
| C | | |
| 0.50 | Euxyl ®K300 | Phenoxyethanol, methylparaben, ethylparaben, ethylparaben, butylparaben, propylparaben and isobutylparaben |

Preparation:

Phase A is heated to melting at ca. 80° C. and homogenized for ca. 3 min; phase B is likewise heated up to ca. 80° C., added to phase A and this mixture is homogenized again. It is then left to cool to room temperature with stirring. Phase C is then added and the mixture is homogenized again.

TABLE 4

Dependency of the sorption equilibrium of the polyacrylate and of the zinc oxide going into solution on the respective pH

| NaOH— addition cumulated, calc. 100% g/kg (suspension) | Retentate (suspension) | | | Permeate (clear) | | | | |
|---|---|---|---|---|---|---|---|---|
| | pH | | org. C | pH | | NaCl | org. C | Zn |
| | T = 60° C. | T = 25° C. | calc. susp. (ppm) | T = 60° C. | T = 25° C. | (%) | (ppm) | (ppm) |
| 0.0 | 7.7 | 8.3 | 740 | 7.7 | 8.4 | 2.50 | 140 | 0 |
| 2.0 | 11.4 | 12.4 | 700 | 11.3 | 12.3 | 2.50 | 590 | 0 |
| 3.5 | 11.6 | 12.6 | 770 | 11.5 | 12.6 | 2.47 | 610 | 10 |
| 5.0 | 11.7 | 12.8 | 760 | 11.7 | 12.8 | 2.49 | 690 | 30 |
| 10.8 | 11.9 | 13.0 | 770 | 11.8 | 13.0 | 2.43 | 710 | 120 |
| 15.0 | 11.9 | 13.0 | 770 | 11.8 | 13.1 | 2.41 | 750 | 230 |

TABLE 6

Depletion of NaCl and free polyacrylate in them retentate during concentration and diafiltration
Membrane: flat membrane 100 kD (polysulfone, Microdyn-Nadir)
Transmembrane pressure TMP = 1 bar, processing temperature PT = 40° C.
Feed: synthesis discharge (ca. 1.6% ZnO, 2.5% NaCl, 0.2% Na polyacrylate PA15 + 0.5% NaOH calc. suspension added before UF)

| Sample | Retentate (suspension) | | | | | | | | | Permeate LF at PT [mS/cm] | Depletion based on ZnO | | UV/Vis After spray-drying with 70° C. outlet temperature + NT at 200° C. | |
|---|---|---|---|---|---|---|---|---|---|---|---|---|---|---|
| | pH at PT | Density [g/l] | SC calc. susp. [%] | NaCl calc. susp. [%] | NaOH calc. susp. [%] | org. C calc. susp. [ppm] | ZnO calc. susp. [%] | NaCl g NaCl/ 100 g ZnO | org. C g org. C/ 100 g ZnO | | NaCl [%] | org. C [%] | T [450 nm] | T [360 nm] |
| Concentration (MK = 11.3) | | | | | | | | | | | | | | |
| MK = 1.00 (start) | 12.3 | 1.015 | 4.8 | 2.47 | 0.50 | 760 | 1.6 | 152 | 4.66 | 69.7 | 0.0 | 0.0 | — | — |
| MK = 11.3 (stop) | 12.4 | 1.238 | 21.2 | 2.01 | 0.41 | 1438 | 18.5 | 10.9 | 0.78 | 86.0 | 92.8 | 83.3 | — | — |
| 2. Diafiltration with demineralized H₂O (MA = 6.00) | | | | | | | | | | | | | | |
| MA = 0 (start) | 12.4 | 1.238 | 21.2 | 2.01 | 0.41 | 1438 | 18.5 | 10.9 | 0.78 | 86.0 | 92.8 | 83.3 | | |
| MA 3 | 10.8 | 1.211 | 17.8 | 0.036 | 0.04 | 720 | 17.5 | 0.21 | 0.41 | 2.10 | 99.9 | 91.2 | 92.5 | 19.9 |

TABLE 6-continued

Depletion of NaCl and free polyacrylate in them retentate during concentration and diafiltration
Membrane: flat membrane 100 kD (polysulfone, Microdyn-Nadir)
Transmembrane pressure TMP = 1 bar, processing temperature PT = 40° C.
Feed: synthesis discharge (ca. 1.6% ZnO, 2.5% NaCl, 0.2% Na polyacrylate PA15 + 0.5% NaOH calc. suspension added before UF)

| Sample | pH at PT | Density [g/l] | Retentate (suspension) SC calc. susp. [%] | NaCl calc. susp. [%] | NaOH calc. susp. [%] | org. C calc. susp. [ppm] | ZnO calc. susp. [%] | NaCl g NaCl/ 100 g ZnO | org. C g org. C/ 100 g ZnO | Permeate LF at PT [mS/cm] | Depletion based on ZnO NaCl [%] | org. C [%] | UV/Vis After spray-drying with 70° C. outlet temperature + NT at 200° C. T [450 nm] | T [360 nm] |
|---|---|---|---|---|---|---|---|---|---|---|---|---|---|---|
| MA 4 | — | 1.207 | 17.8 | 0.025 | n.d. | 740 | 17.6 | 0.14 | 0.42 | 0.90 | 99.9 | 91.0 | 92.3 | 19.8 |
| MA 5 | 10.5 | 1.206 | 18.0 | 0.022 | n.d. | 750 | 17.9 | 0.12 | 0.42 | 0.55 | 99.9 | 91.0 | 92.6 | 20.1 |
| MA = 6 (stop) | 10.3 | 1.210 | 17.6 | 0.026 | n.d. | 660 | 17.4 | 0.15 | 0.38 | 0.29 | 99.9 | 91.9 | 92.4 | 19.6 | n.d. = not detectable

TABLE 7

Influence of the pH on the acrylate depletion

| ZnO synthesis: | |
|---|---|
| Conditions: | Stirred-tank reactor, 60° C., 2 h afterstirring time |
| Initial charge: | ZnCl2 = 0.2 mol/kg adjusted to pH = 5 with HCl |
| Feed: | NaOH = 0.4 mol/kg + 4 g of PA15 (calc. 100%) |
| pH: | Measured after synthesis at 25° C. = 10.8 |
| Ultrafiltration: | |
| Conditions: | TMP = 1 bar, T = 60° C. |
| Membrane: | Polyether sulfone, 300 kD (Sartorius) |
| Feed: | in each case ca. 16 kg of the same synthesis suspension |
| Concentration: | MK = 8 (retentate = 2 kg) |
| Diafiltration: | with demineralized water (dem. water), MA = 5 |

| Experiment | pH increased before UF with NaOH | Filtration Concentration Start pH (60° C.) | MK | Diafiltration Start pH (60° C.) | MA | Discharge End pH (60° C.) | ZnO (%) | pH (RT) | Content/100 g ZnO NaCl | org. C total | UV/Vis After spray-drying with 60° C. outlet temperature + after-heat treatment at 180° C. T(450 nm) | T(360 nm) |
|---|---|---|---|---|---|---|---|---|---|---|---|---|
| 44 | no | 9.9 | 8.1 | 9.9 | 5.0 | 9.2 | 14.7 | 9.9 | 0.16 | 2.04 | 94.0 | 45.4 |
| 46 | yes | 11.1 | 7.9 | 11.1 | 5.0 | 10.1 | 14.1 | 10.9 | 0.14 | 1.45 | 94.0 | 25.8 |
| 47 | yes | 12.0 | 8.1 | 12.0 | 5.0 | 10.5 | 12.9 | 11.4 | 0.20 | 0.50 | 93.2 | 21.2 |

The invention claimed is:

1. A process for the preparation of surface-modified nanoparticulate zinc oxide particles comprising the steps
   a) preparation of a solution comprising water and at least one zinc salt (solution 1) and a solution comprising water and at least one strong base (solution 2), where at least one of the two solutions 1 and 2 comprises at least one polyacrylate, wherein the polycrylate is a salt of a homopolymer of acrylic acid and has a $M_w$ in the range of from 1000 to 20000 g/mol;
   b) mixing the solutions 1 and 2 prepared in step a), during which the surface-modified nanoparticulate particles are formed and precipitate out of the solution to form an aqueous suspension,
   c) concentration of the aqueous suspension of the surface-modified nanoparticulate particles obtained in step b) by membrane filtration, where the pH of the suspension obtained in step b) and to be conveyed to step c) is in a range from 9.8 to 13, and wherein the zinc oxide concentration of the suspension obtained in step b) of zinc oxide particles in step c) is increased through membrane filtration to a value in the range from 5 to 40% by weight of zinc oxide;
   d) optional purification of the concentrated aqueous suspension of the surface-modified nanoparticulate particles obtained in step c),
   e) optionally drying of the surface-modified nanoparticulate particles obtained in step d) and
   f) optional thermal after treatment of the dried, surface-modified nanoparticulate particles obtained in step e).

2. The process according to claim 1, wherein the zinc salt is zinc chloride, zinc nitrate or zinc acetate.

3. The process according to claim 1, wherein the strong base is an alkali metal hydroxide, an alkaline earth metal hydroxide or ammonia.

4. The process according to claim 1, wherein step b) takes place at a temperature in the range from 40° C. to 80° C.

5. The process according to claim 1, wherein solution 1 is in the reactor in which the precipitation of the zinc oxide takes place, and at the start of step b) solution 2 is added to solution 1.

6. The process according to claim 1, wherein step c) comprises the evaporation of water.

7. The process according to claim 1, wherein the pH of the suspension of zinc oxide particles obtained in step b) and to be conveyed to step c) is adjusted to a pH in the range from 10 to 13.

8. The process according to claim 1, wherein step d) comprises at least a first diafiltration with an alkaline solution and at least a second diafiltration with water.

9. The process according to claim 1, wherein step f) is or comprises a heating of the dried, surface-modified nanoparticulate particles obtained in step e) at temperatures in the range from 150 to 250° C.

10. A process for the preparation of aqueous suspensions of surface-modified nanoparticulate zinc oxide particles comprising steps a) to c) or a) to d) of the process according to claim 1, wherein a dispersant is added to the aqueous suspension before or during step c).

\* \* \* \* \*